United States Patent
Perricone

(10) Patent No.: US 12,064,467 B2
(45) Date of Patent: Aug. 20, 2024

(54) SYSTEMS AND METHODS FOR DELIVERY OF HUMANIN OR OTHER PEPTIDES

(71) Applicant: Transdermal Biotechnology, Inc., Meriden, CT (US)

(72) Inventor: Nicholas V. Perricone, Madison, CT (US)

(73) Assignee: Transdermal Biotechnology, Inc., Meriden, CT (US)

( * ) Notice: Subject to any disclaimer, the term of this patent is extended or adjusted under 35 U.S.C. 154(b) by 0 days.

(21) Appl. No.: 17/975,950

(22) Filed: Oct. 28, 2022

(65) Prior Publication Data

US 2024/0156900 A1 May 16, 2024

(51) Int. Cl.
| | |
|---|---|
| A61K 38/17 | (2006.01) |
| A61K 9/00 | (2006.01) |
| A61K 31/685 | (2006.01) |
| A61K 47/14 | (2017.01) |
| A61K 47/18 | (2017.01) |
| A61K 47/24 | (2006.01) |

(52) U.S. Cl.
CPC ........ *A61K 38/1709* (2013.01); *A61K 9/0014* (2013.01); *A61K 31/685* (2013.01); *A61K 47/14* (2013.01); *A61K 47/183* (2013.01); *A61K 47/24* (2013.01)

(58) Field of Classification Search
CPC .............. A61K 38/1709; A61K 9/0014; A61K 31/685; A61K 47/14; A61K 47/183; A61K 47/24
See application file for complete search history.

(56) References Cited

U.S. PATENT DOCUMENTS

| | | |
|---|---|---|
| 7,182,956 B2 | 2/2007 | Perricone et al. |
| 7,611,893 B2 | 11/2009 | Mascarenhas |
| 7,998,928 B2 | 8/2011 | Cohen et al. |
| 8,273,711 B2 | 9/2012 | Perricone |
| 8,435,942 B2 | 5/2013 | Perricone et al. |
| 8,637,470 B2 | 1/2014 | Cohen et al. |
| 8,668,937 B2 | 3/2014 | Perricone et al. |
| 8,709,734 B2 | 4/2014 | Leroy |
| 9,241,899 B2 | 1/2016 | Perricone |
| 9,295,636 B2 | 3/2016 | Perricone |
| 9,295,637 B2 | 3/2016 | Perricone |
| 9,295,647 B2 | 3/2016 | Perricone |
| 9,314,422 B2 | 4/2016 | Perricone |
| 9,314,423 B2 | 4/2016 | Perricone |
| 9,314,433 B2 | 4/2016 | Perricone |
| 9,320,706 B2 | 4/2016 | Perricone |
| 9,320,758 B2 | 4/2016 | Perricone |
| 9,339,457 B2 | 5/2016 | Perricone |
| 9,387,159 B2 | 7/2016 | Perricone |
| 9,687,520 B2 | 6/2017 | Perricone |
| 9,937,227 B2 | 4/2018 | Perricone |
| 10,172,953 B2 | 1/2019 | Schellenberger et al. |
| 10,391,143 B2 | 8/2019 | Cohen et al. |
| 10,751,417 B2 | 8/2020 | Adams et al. |
| 10,792,331 B2 | 10/2020 | Wang et al. |
| 2004/0225004 A1* | 11/2004 | Zeligs ................. A61K 31/195 514/564 |
| 2011/0123577 A1 | 5/2011 | Perricone et al. |
| 2013/0123168 A1 | 5/2013 | Cohen et al. |
| 2013/0330380 A1 | 12/2013 | Perricone et al. |
| 2014/0271742 A1 | 9/2014 | Perricone |
| 2020/0181197 A1* | 6/2020 | Cundy ...................... A61P 1/00 |

FOREIGN PATENT DOCUMENTS

| | | |
|---|---|---|
| WO | WO 2006/019365 A1 | 2/2006 |
| WO | WO 2011/076880 A1 | 6/2011 |
| WO | WO 2011/104708 A1 | 9/2011 |
| WO | WO 2013/074871 A2 | 5/2013 |
| WO | WO 2013/162718 A2 | 10/2013 |
| WO | WO 2014/159986 A2 | 10/2014 |

(Continued)

OTHER PUBLICATIONS

Bryant et al. Dmt and Opioid Peptides: A Potent Alliance. Biopolymers (Peptide Science), vol. 71, pp. 86-102 (Year: 2003).*
Shanker et al. Amino Acid and Peptide-Based Liquid Crystals: An Overview. Current Organic Synthesis, 17 (4), 2020, pp. 333-350. (Year: 2020).*
Rapalli et al. Insights of lyotropic liquid crystals in topical drug delivery for targeting various skin disorder. J Mol Liquis, 2020, 315, 113771, pp. 1-12. (Year: 2020).*
Wang et al., Cytoprotective role of S14G-humanin (HNG) in ultraviolet-B induced epidermal stem cells injury. Biomed Pharmacother. Feb. 2019;110:248-253. doi: 10.1016/j.biopha.2018.11.059. Epub Nov. 30, 2018.
Yen et al., The mitochondrial derived peptide humanin is a regulator of lifespan and healthspan. Aging (Albany NY). Jun. 23, 2020;12(12):11185-11199. doi: 10.18632/aging.103534. Epub Jun. 23, 2020.

(Continued)

*Primary Examiner* — Marcela M Cordero Garcia
(74) *Attorney, Agent, or Firm* — Wolf, Greenfield & Sacks, P.C.

(57) ABSTRACT

The present disclosure generally relates to systems and methods for delivering humanin and/or other peptides to a subject. In some cases, these may be used for treating or preventing aging skin, or for other diseases. Non-limiting examples of other peptides include mitochondrial-derived peptides such as HNG or MOTS-c. In addition, certain embodiments are generally directed to treatments that can be delivered using topical compositions applied to the skin. For example, in some cases, the composition includes lecithin and/or other components that may facilitate delivery through the skin. Further, certain embodiments may include active ingredients such as tributyrin or 2,6-dimethyl-L-tyrosine, which may interact with humanin or other peptides. Compositions such as these may be used in certain embodiments, for example, to reduce inflammation within the skin, or as an anti-aging treatment, etc. Other aspects are generally directed to methods of making or using such compositions, methods of promoting such compositions, kits including such compositions, or the like.

18 Claims, No Drawings

Specification includes a Sequence Listing.

(56) References Cited

FOREIGN PATENT DOCUMENTS

| WO | WO 2014/160016 A2 | 10/2014 |
| WO | WO 2014/160047 A2 | 10/2014 |
| WO | WO 2014/160070 A2 | 10/2014 |
| WO | WO 2014/160102 A2 | 10/2014 |
| WO | WO 2014/160103 A2 | 10/2014 |
| WO | WO 2014/160138 A2 | 10/2014 |
| WO | WO 2014/160145 A2 | 10/2014 |
| WO | WO 2014/160187 A1 | 10/2014 |
| WO | WO 2016/040953 A1 | 3/2016 |
| WO | WO 2022/003673 A1 | 1/2022 |

OTHER PUBLICATIONS

Zapala et al., Humanins, the neuroprotective and cytoprotective peptides with antiapoptotic and anti-inflammatory properties. Pharmacol Rep. Sep.-Oct. 2010;62(5):767-77.

* cited by examiner

SEQUENCE LISTING

```
Sequence total quantity: 11
SEQ ID NO: 1            moltype = AA  length = 21
FEATURE                 Location/Qualifiers
source                  1..21
                        mol_type = protein
                        organism = Synthetic construct
SEQUENCE: 1
MAPRGFSCLL LLTSEIDLPV K                                                   21

SEQ ID NO: 2            moltype = AA  length = 24
FEATURE                 Location/Qualifiers
source                  1..24
                        mol_type = protein
                        organism = Synthetic construct
SEQUENCE: 2
MAPRGFSCLL LLTSEIDLPV KRRA                                                24

SEQ ID NO: 3            moltype = AA  length = 21
FEATURE                 Location/Qualifiers
source                  1..21
                        mol_type = protein
                        organism = Synthetic construct
SEQUENCE: 3
MAPRGFSCLL LLTGEIDLPV K                                                   21

SEQ ID NO: 4            moltype = AA  length = 24
FEATURE                 Location/Qualifiers
source                  1..24
                        mol_type = protein
                        organism = Synthetic construct
SEQUENCE: 4
MAPRGFSCLL LLTGEIDLPV KRRA                                                24

SEQ ID NO: 5            moltype = AA  length = 16
FEATURE                 Location/Qualifiers
source                  1..16
                        mol_type = protein
                        organism = Synthetic construct
SEQUENCE: 5
MRWQEMGYIF YPRKLR                                                         16

SEQ ID NO: 6            moltype = AA  length = 24
FEATURE                 Location/Qualifiers
source                  1..24
                        mol_type = protein
```

```
                        organism = Synthetic construct
SEQUENCE: 6
MCHWAGGASN TGDARGDVFG KQAG                                              24

SEQ ID NO: 7            moltype = AA  length = 26
FEATURE                 Location/Qualifiers
source                  1..26
                        mol_type = protein
                        organism = Synthetic construct
SEQUENCE: 7
MGVKFFTLST RFFPSVQRAV PLWTNS                                            26

SEQ ID NO: 8            moltype = AA  length = 38
FEATURE                 Location/Qualifiers
source                  1..38
                        mol_type = protein
                        organism = Synthetic construct
SEQUENCE: 8
MLGYNFSSFP CGTISIAPGF NFYRLYFIWV NGLAKVVW                                38

SEQ ID NO: 9            moltype = AA  length = 26
FEATURE                 Location/Qualifiers
source                  1..26
                        mol_type = protein
                        organism = Synthetic construct
SEQUENCE: 9
MLEVMFLVNR RGKICRVPFT FFNLSL                                            26

SEQ ID NO: 10           moltype = AA  length = 24
FEATURE                 Location/Qualifiers
source                  1..24
                        mol_type = protein
                        organism = Synthetic construct
SEQUENCE: 10
MYCSEVGFCS EVAPTEIFNA GLVV                                              24

SEQ ID NO: 11           moltype = AA  length = 20
FEATURE                 Location/Qualifiers
source                  1..20
                        mol_type = protein
                        organism = Synthetic construct
SEQUENCE: 11
MLDQDIPMVQ PLLKVRLFND                                                   20
```

SYSTEMS AND METHODS FOR DELIVERY OF HUMANIN OR OTHER PEPTIDES

REFERENCE TO A SEQUENCE LISTING SUBMITTED AS AN XML FILE VIA PATENT CENTER

The instant application contains a Sequence Listing which has been submitted in XML format via Patent Center and is hereby incorporated by reference in its entirety. Said XML copy, created on Mar. 10, 2023, is named T067970053US00-SEQ-TC and is 10,548 bytes in size.

FIELD

The present disclosure generally relates to systems and methods for delivering humanin and/or other peptides to a subject. In some cases, these may be used for treating or preventing aging skin, or for other diseases.

BACKGROUND

Aging skin is a problem that happens to everyone over time. Common symptoms of aging skin include a loss of elasticity, creases and wrinkles, age spots, and the like. Skin ages due to a variety of factors in addition to age. These include, for example, various environmental factors such as humidity, ultraviolet radiation, occupation, exposure to chemicals, moisture, and the like. Despite interest in the subject throughout must of human history, aging skin nonetheless remains an unsolved problem, and improvements are thus still needed.

SUMMARY

The present disclosure generally relates to systems and methods for delivering humanin and/or other peptides to a subject. The subject matter of the present disclosure involves, in some cases, interrelated products, alternative solutions to a particular problem, and/or a plurality of different uses of one or more systems and/or articles.

One aspect is generally drawn to a composition for topical delivery. In one set of embodiments, the composition comprises a topical formulation comprising humanin and lecithin. In another set of embodiments, the composition comprises a topical formulation comprising a humanin-related peptide and lecithin. The composition, according to yet another set of embodiments, is generally drawn to a topical formulation comprising a mitochondrial-derived peptide and lecithin. In still another set of embodiments, the composition is generally drawn to a topical formulation comprising tributyrin and lecithin. In another set of embodiments, the composition comprises a topical formulation comprising HNG and lecithin. In still another set of embodiments, the composition comprises a topical formulation comprising 2,6-dimethyl-L-tyrosine and lecithin.

Another aspect is generally drawn to a method. According to one set of embodiments, the method comprises applying, to the skin of a subject, a topical composition comprising humanin and lecithin. The method, in another set of embodiments, comprises applying, to the skin of a subject, a topical composition comprising a humanin-related peptide and lecithin. In yet another set of embodiments, the method comprises applying, to the skin of a subject, a topical composition comprising a mitochondrial-derived peptide and lecithin. The method, in still another set of embodiments, comprises applying, to the skin of a subject, a topical composition comprising tributyrin and lecithin. According to another set of embodiments, the method comprises applying, to the skin of a subject, a topical composition comprising HNG and lecithin. In accordance with still another set of embodiments, the method comprises applying, to the skin of a subject, a topical composition comprising 2,6-dimethyl-L-tyrosine and lecithin.

Several methods are disclosed herein of administering a subject with a compound for prevention or treatment of a particular condition. It is to be understood that in each such aspect of the disclosure, the disclosure specifically includes, also, the compound for use in the treatment or prevention of that particular condition, as well as use of the compound for the manufacture of a medicament for the treatment or prevention of that particular condition.

In another aspect, the present disclosure encompasses methods of making one or more of the embodiments described herein. In still another aspect, the present disclosure encompasses methods of using one or more of the embodiments described herein.

Other advantages and novel features of the present disclosure will become apparent from the following detailed description of various non-limiting embodiments of the disclosure.

---

BREIF DESCRIPTION OF THE SEQUENCES

SEQ ID NO: 1 is
MAPRGFSCLLLLTSEIDLPVK;

SEQ ID NO: 2 is
MAPRGFSCLLLLTSEIDLPVKRRA;

SEQ ID NO: 3 is
MAPRGFSCLLLLTGEIDLPVK;

SEQ ID NO: 4 is
MAPRGFSCLLLLTGEIDLPVKRRA;

SEQ ID NO: 5 is
MRWQEMGYIFYPRKLR;

SEQ ID NO: 6 is
MCHWAGGASNTGDARGDVFGKQAG;

SEQ ID NO: 7 is
MGVKFFTLSTRFFPSVQRAVPLWTNS;

SEQ ID NO: 8 is
MLGYNFSSFPCGTISIAPGFNFYRLYFIWVNGLAKVVW;

SEQ ID NO: 9 is
MLEVMFLVNRRGKICRVPFTFFNLSL;

SEQ ID NO: 10 is
MYCSEVGFCSEVAPTEIFNAGLVV;
and

SEQ ID NO: 11 is
MLDQDIPMVQPLLKVRLEND.

---

DETAILED DESCRIPTION

The present disclosure generally relates to systems and methods for delivering humanin and/or other peptides to a subject. In some cases, these may be used for treating or preventing aging skin, or for other diseases. Non-limiting examples of other peptides include mitochondrial-derived peptides such as HNG or MOTS-c. In addition, certain embodiments are generally directed to treatments that can be delivered using topical compositions applied to the skin. For example, in some cases, the composition includes lecithin and/or other components that may facilitate delivery through the skin. Further, certain embodiments may include active ingredients such as tributyrin or 2,6-dimethyl-L-tyrosine, which may interact with humanin or other peptides. Compositions such as these may be used in certain embodiments, for example, to reduce inflammation within the skin, or as an anti-aging treatment, etc. Other aspects are generally directed to methods of making or using such compositions, methods of promoting such compositions, kits including such compositions, or the like.

For example, some aspects of the present disclosure are generally directed to topical compositions which can be applied to the skin of a subject, e.g., a human subject. The topical compositions may contain components that may be used for various applications, including treating aging skin or protecting against sunburn, etc. Examples of such components include humanin or humanin-related peptides such as HNG, tributyrin, 2,6-dimethyl-L-tyrosine, or the like, including any of those described in detail herein. The compositions may also include, in certain embodiments, a formulation that allows for the delivery of such components into the skin. For example, the composition may include lecithin, which may be present in liposomes, micelles, or other vesicles containing peptides or other components. The composition can take the form of a gel, a cream, a lotion, an ointment, a solution, a solid "stick," etc., that can be rubbed or sprayed onto the skin. The composition can also be applied to a mucosal surface in some instances.

In one aspect, the composition comprises humanin and/or a humanin-related peptide, such as HNG or small humanin-like peptides (SHLP) 1-6. One or more than one such peptide may be present. Humanin (and related peptides) may have various neuroprotective or cytoprotective effects, in accordance with certain embodiments. For instance, such peptides may be useful as a treatment for neurodegenerative diseases such as Alzheimer's disease, Huntington's disease, prion disease, or stroke. In addition, such peptides may offer protective effects against diseases such as oxidative stress, atherosclerotic plaque formation, or heart attack. In some cases, such peptides can have certain metabolic effects, for example, with pancreatic beta-cells or insulin sensitivity, which may be helpful with diabetes treatment.

Humanin can appear as a 21-amino acid peptide (e.g., having a sequence MAPRGFSCLLLLTSEIDLPVK, SEQ ID NO. 1) or a 24-amino acid peptide (e.g., having a sequence MAPRGFSCLLLLTSEIDLPVKRRA, SEQ ID NO. 2). Both peptides have similar effects. In addition, humanin-related peptides similar to these can also be used, e.g., in addition and/or instead of a humanin peptide. For example, a humanin-related peptide may include peptides that have 1, 2, or 3 amino acid substitutions from one of the humanin sequences.

As a non-limiting example, HNG (humanin G) is a S 14G derivative of humanin, e.g., where the "S" (serine) in the 14th position of the peptide is replaced by "G" (glycine), thus resulting in MAPRGFSCLLLLTGEIDLPVK (SEQ ID NO. 3) or MAPRGFSCLLLLTGEIDLPVKRRA (SEQ ID NO. 4). In some cases, HNG may have similar effects as humanin, and in certain embodiments, HNG may also be more efficacious than humanin.

As another non-limiting example, a humanin-related peptide may be a SHLP (small humanin-like peptides). In some cases, SHLPs may be able to regulate cell viability and/or mitochondrial function. Examples of these include SHLP1-SHLP6, which are as follows:

```
SHLP1
                                          (SEQ ID NO: 6)
MCHWAGGASNTGDARGDVFGKQAG

SHLP2
                                          (SEQ ID NO: 7)
MGVKFFTLSTRFFPSVQRAVPLWINS

SHLP3
                                          (SEQ ID NO: 8)
MLGYNFSSFPCGTISIAPGFNFYRLYFIWVNGLAKVVW

SHLP4
                                          (SEQ ID NO: 9)
MLEVMFLVNRRGKICRVPFTFFNLSL

SHLP5
                                          (SEQ ID NO: 10)
MYCSEVGFCSEVAPTEIFNAGLVV

SHLP6
                                          (SEQ ID NO: 11)
MLDQDIPMVQPLLKVRLEND.
```

Thus, in one set of embodiments, a composition such as described herein may be given to a subject, e.g., a subject having or at risk for a neurodegenerative disease. In another set of embodiments, a composition such as described herein may be given to a subject having or at risk of oxidative stress. For example, in some cases, humanin and/or a humanin-related peptide may affect the inflammatory cascade pathways within the skin, and thus compositions such as those described herein may be used to treat aging within the skin. Without wishing to be bound by any theory, it is believed that inflammation within the skin may cause the effects of aging within the skin, such as sagging, loss of elasticity or integrity, discoloration, etc.; humanin and/or similar peptides may be useful reduce inflammation within the skin, thereby slowing down the aging process within the skin. Accordingly, in some embodiments, compositions such as those described herein may be applied topically to the skin of the subject as an anti-aging treatment.

In addition, in certain aspects, other active ingredients may be present as well, e.g., in addition to humanin and/or humanin-related peptides. For example, in one set of embodiments, a composition may comprise tributyrin. Tributyrin is a triglyceride having a structure:

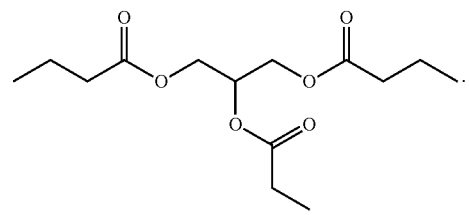 [SMILES: CCCC(=O)OCC(COC(=O)CCC)OC(=O)CC]

In some embodiments, a composition comprising tributyrin and humanin and/or a humanin-related peptide such as HNG may be useful for treating oxidative stress in a subject. For example, such compositions may inhibit upregulation of TNF-alpha, which is part of a response to ultraviolet B (UVB) light. Accordingly, such compositions may be useful for treat aging skin, ultraviolet radiation or sunburn, and/or for reducing inflammation in a subject, etc.

In addition, in certain aspects, other mitochondrial-derived peptides may be present in certain embodiments, e.g., in addition to and/or instead of humanin. In general, mitochondrial-derived peptides are peptides encoded within a cell by mitochondrial DNA (as opposed to nuclear DNA). In some cases, the mitochondrial-derived peptides (MDPs) may be encoded by short open-reading frames (sORF) in mitochondrial DNA. Examples of mitochondrial-derived peptides include MOTS-c and humanin or humanin-related peptides, such as small humanin-like peptides (SHLP) 1-6.

For example, MOTS-c stands for mitochondrial ORF of the twelve S c, and has a sequence MRWQEMGYIFY-PRKLR (SEQ ID NO: 5). It may target muscle cells and/or enhance glucose metabolism. Thus, in some cases, compositions comprising MOTS-c may be given to a subject, e.g., a subject having or at risk of obesity, diabetes, aging, or the like.

As mentioned, in some aspects, components such as those described above may be present within a composition comprising a lecithin, such as phosphatidylcholine. The composition may be a cream or other formulations such as those described herein. In one set of embodiments, the composition may comprise liquid crystal multilamellar phosphatidylcholine. In some cases, the compositions are relatively free of oxygen ($O_2$) or water. Without wishing to be bound by any theory, it is believed that such compositions may serve to inhibit or reduce reaction of components within the composition from reacting with oxygen (e.g., in the air, or dissolved in water, etc.). Thus, in some cases, the compositions may be stable, and/or can be stored for periods of time with little or no loss or reaction of the components contained therein. In some cases, stability of the composition can be achieved at room temperature (about 25° C.), and/or at other storage temperatures such as those described herein.

In one set of embodiments, the composition comprises a first phase comprising a lecithin such as phosphatidylcholine, which may be present within a second phase. The composition may also comprise an emulsifier, such as is discussed herein. Other components, for example, transdermal penetration enhancers, adjuvants, surfactants, lubricants, etc. can also be present in certain cases.

The compositions comprise, in certain embodiments, a phase comprising phosphatidylcholine and/or other lecithins in which the components may be contained within, e.g., to reduce the ability of oxygen (e.g., from the air) to react with such components. In some cases, the phosphatidylcholine or lecithin may be contained within a second phase. In some cases, the composition may have phosphatidylcholine or lecithin in the form of vesicles, e.g., micelles or liposomes. The phosphatidylcholine or lecithin composition can be unilamellar or multilamellar in some embodiments. However, in some instances, the phosphatidylcholine or lecithin may be present as a liquid crystal arrangement, rather than a vesicular or liposomal arrangement.

In some cases, certain components may be contained within water or other aqueous environment within the composition (e.g., within vesicles such as liposomes or an emulsion or a liquid crystal structure within the composition, etc.), although in some embodiments, little or no water is used, and some or all of the components are directly contained within the phosphatidylcholine or other lecithin within the composition.

In certain embodiments, the composition, or at least a phase of the composition (e.g., containing pyruvic acid and/or pyruvate and/or antioxidants) is substantially free of water, e.g., comprising no more than about 10 wt %, no more than about 3 wt %, no more than about 1 wt %, no more than about 0.3 wt %, or no more than about 0.1 wt % water (i.e., relative to the weight of the overall composition). The composition may also have no more than about 1,000 ppm, no more than about 750 ppm, no more than about 500 ppm, no more than about 400 ppm, no more than about 300 ppm, no more than about 250 ppm, no more than about 200 ppm, no more than about 150 ppm, no more than about 100 ppm, no more than about 50 ppm, no more than about 25 ppm, or no more than about 10 ppm of water (by weight). In certain embodiments, no detectable water may be present in the composition, or at least within one phase of the composition. Any suitable technique can be used for determining the amount of water present in the composition, for example, Karl-Fisher titration. In some cases, the composition may also be free of any liquids that typically contain water, e.g., physiological buffers, bodily fluids, saline, blood, or the like.

In addition, in some embodiments, the composition is substantially free of gaseous oxygen (02). For instance, the composition may also have no more than about 1,000 ppm, no more than about 750 ppm, no more than about 500 ppm, no more than about 400 ppm, no more than about 300 ppm, no more than about 250 ppm, no more than about 200 ppm, no more than about 150 ppm, no more than about 100 ppm, no more than about 50 ppm, no more than about 25 ppm, or no more than about 10 ppm of oxygen (by weight).

Phosphatidylcholine (herein abbreviated "PC") is a basic component of cell membrane bilayers and the main phospholipid circulating in the plasma of blood. Phosphatidylcholine typically has a phospholipid structure with a choline head group and a glycerophosphoric acid tail group. The tail group can be saturated or unsaturated. More than one tail group may be present in the phosphatidylcholine in some cases, and the tail groups may be the same or different. Specific non-limiting examples of phosphatidylcholines that could be used include one or a mixture of stearic, palmitic, margaric, and/or oleic acid diglycerides linked to a choline ester head group.

Phosphatidylcholines are a member of a class of compounds called lecithins. Typically, a lecithin is a composed of phosphoric acid, choline, fatty acids, glycerol, glycolipids, triglycerides, and/or phospholipids. In some cases, other lecithins may be used, in addition to or instead of a phosphatidylcholine. Non-limiting examples of other lecithins include phosphatidylethanolamine, phosphatidylinositol, or phosphatidic acid. Many commercial lecithin products are available, such as, for example, Lecithol®, Vitellin®, Kelecin®, and Granulestin®. Lecithin is widely used in the food industry. In some embodiments, certain compositions can contain synthetic or natural lecithin, or mixtures thereof. Natural preparations are used in some cases because they exhibit desirable physical characteristics, and/or may be economical or nontoxic. However, in other embodiments, non-natural preparations are used, or the composition can include both natural and non-natural preparations.

Any suitable amount of phosphatidylcholine or lecithin may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the entire composition can be a phosphatidylcholine or a lecithin. In some cases, the phosphatidylcholine or lecithin may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the phosphatidylcholine or lecithin may be present at between about 8 wt % and about 65 wt %, or between about 0 wt % and about 10 wt %, etc. One or more than one type of phosphatidylcholine or lecithin may be present.

In some embodiments, the composition comprises a phosphatidylcholine, e.g., any of those described herein. The composition can include any suitable amount of phosphatidylcholine, for example, at least about 1 wt %, at least about 3 wt %, at least about 5 wt %, at least about 10 wt %, at least about 20 wt %, at least about 30 wt %, at least about 40 wt %, at least about 50 wt %, at least about 60 wt %, at least about 70 wt %, at least about 80 wt %, at least about 90 wt % etc. In some cases, no more than about 90 wt %, no more than about 80 wt %, no more than about 70 wt %, no more than about 60 wt %, no more than about 50 wt %, no more than about 40 wt %, no more than about 30 wt %, no more than about 20 wt %, no more than about 10 wt %, or no more than about 5 wt % of the composition is phosphatidylcholine. Combinations of any of these are also possible. For example, the composition may be between about 0 wt % and about 10 wt % phosphatidylcholine. The composition may include one or more than one phosphatidylcholine. One non-limiting example of a phosphatidylcholine is Phospholipon-90G (American Lecithin Company).

Some compositions may contain polyenylphosphatidylcholine (herein abbreviated "PPC"). In some cases, PPC can be used to enhance epidermal penetration. The term "polyenylphosphatidylcholine," as used herein, means any phosphatidylcholine bearing two fatty acid moieties, wherein at least one of the two fatty acids is an unsaturated fatty acid with at least two double bonds in its structure, such as linoleic acid.

Certain types of soybean lecithin and soybean fractions, for example, can contain higher levels of polyenylphosphatidylcholine, with dilinoleoylphosphatidylcholine (18:2-18:2 phosphatidylcholine) as the most abundant phosphatidylcholine species therein, than conventional food grade lecithin. Such lecithins may be useful in formulating certain delivery compositions. In some embodiments, conventional soybean lecithin may be enriched with polyenylphosphatidylcholine, for instance, by adding soybean extracts containing high levels of polyenylphosphatidylcholine. As used herein, this type of phosphatidylcholine is called "polyenylphosphatidylcholine-enriched" phosphatidylcholine (hereinafter referred to as PPC-enriched phosphatidylcholine), even where the term encompasses lecithin obtained from natural sources exhibiting polyenylphosphatidylcholine levels higher than ordinary soybean varieties. These products are commercially available, for example, from American Lecithin Company, Rhone-Poulenc and other lecithin vendors. American Lecithin Company markets its products with a "U" designation, indicating high levels of unsaturation; Rhone-Poulenc's product is a soybean extract containing about 42% dilinoleoylphosphatidylcholine and about 24% palmitoyllinoleylphosphatidylcholine (16:0 to 18:2 of PC) as the major phosphatidylcholine components. Another example of a suitable polyenylphosphatidylcholine is NAT 8729 (also commercially available from vendors such as Rhone-Poulenc and American Lecithin Company).

In some embodiments, various compositions are formulated to be substantially clear or substantially transparent. Transparency may be useful, for instance, for product acceptance in the marketplace, e.g., when applied to the skin of a subject. However, in other embodiments, the composition is not necessarily transparent. Certain substances can be useful in providing a substantially transparent composition, for example, fatty acid esters such as ascorbate palmitate or isopropyl palmitate. In one set of embodiments, the composition may be substantially transparent such that incident visible light (e.g., have wavelengths of between about 400 nm and about 700 nm) can be transmitted through 1 cm of the composition with a loss in intensity of no more than about 50%, about 60%, about 70%, about 80%, or about 90% relative to the incident light. In some embodiments, there may be no substantial difference in the wavelengths that are absorbed by the composition (i.e., white light passing through the composition appears white), although in other cases, there can be more absorption at various wavelengths (for example, such that white light passing through the composition may appear colored).

Other components may also be present within the composition, in accordance with certain embodiments. For example, the composition may include volatile organic fluids, fatty acids, volatile aromatic cyclic compounds, high molecular weight hydrocarbons, or the like.

Any suitable amount of polyenylphosphatidylcholine or lecithin may be present within the composition. For example, at least about 0.25 wt %, at least about 0.5 wt %, at least about 1 wt %, at least about 2 wt %, at least about 3 wt %, at least about 5 wt %, at least about 8 wt %, at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the composition can be polyenylphosphatidylcholine or lecithin. In some cases, the polyenylphosphatidylcholine or lecithin may be present at a concentration of no more than about 95 wt %, no more than about 90 wt %, no more than about 80 wt %, no more than about 70 wt %, no more than about 65 wt %, no more than about 60 wt %, no more than about 50 wt %, no more than about 40 wt %, no more than about 30 wt %, no more than about 20 wt %, or no more than about 10%. Combinations of any of these are also possible. For instance, the polyenylphosphatidylcholine or lecithin may be present at between about 8 wt % and about 65 wt %. In some embodiments, at least about 20 wt %, at least about 30 wt %, at least about 40 wt %, at least about 50 wt %, at least about 60 wt %, at least about 70 wt %, at least about 80 wt %, at least about 90 wt %, or about 100 wt % of all of the phosphatidylcholine or lecithin in the composition is polyenylphosphatidylcholine.

While not wishing to be bound to any theory, it is believed that the PPC-enriched phosphatidylcholine may contribute to the stability of the composition, and/or by enhancing its penetration into the skin or other area, e.g., a mucosal surface.

In certain embodiments, a composition such as those described herein can be formulated to include a first phase and a second phase. Typically, the second phase is substantially immiscible with the first phase comprising phosphatidylcholine or lecithin. Two phases that are substantially immiscible are able to form discrete phases when exposed to each other at ambient conditions (e.g., 25° C. and 1 atm) for extended periods of time (e.g., at least about a day). The phases can be separate identifiable phases (e.g., one may float above the other), or in some cases, the phases are intermingled, e.g., as in an emulsion. The stability of the discrete phases may be kinetic and/or thermodynamic in nature, in various embodiments.

In one set of embodiments, an emulsifier may be present, and in some cases, the emulsifier may cause the first phase comprising phosphatidylcholine or lecithin to form a liquid crystal, and/or vesicles such as micelles or liposomes. In some cases, multilamellar structures may be present within the liquid crystal phase, although in other cases, only unilamellar structures may be present. For example, in certain cases, the PPC-enriched phosphatidylcholine can be loosely arranged in a multilamellar fashion. In some cases, the first phase (e.g., comprising PPC-enriched phosphatidylcholine) and the second phase can form a structure such as is disclosed in U.S. Pat. No. 7,182,956 to Perricone, et al. This is believed (without wishing to be bound by any theory) to form a loosely arranged, yet stable, PPC-enriched phosphatidylcholine-drug complex that may allow penetration and delivery of components and optional adjunct ingredients to the skin.

The emulsifier, in one embodiment, may be a substance that is able to stabilize an emulsion by increasing its kinetic stability. The emulsifier may also be chosen in some cases to be relatively inert or non-toxic relative to the skin or to a mucosal surface.

A variety of emulsifiers can be used, and many emulsifiers are readily available commercially. In one embodiment, for example, the emulsifier comprises a surfactant. Non-limiting examples of surfactants include a siloxylated polyether comprising dimethyl, methyl(propylpolyethylene oxide propylene oxide, acetate) siloxane commercially available from vendors such as Dow Corning (Dow Corning 190 surfactant). Other examples of materials that can be used as (or within) the second phase (e.g., as emulsifiers) include, but are not limited to, 1,2-propanediol, or silicone fluids containing low viscosity polydimethylsiloxane polymers, methylparaben (p-hydroxy benzoic acid methyl ester) commercially available from vendors such as Dow Corning (Dow Corning 200 silicone fluid). Still other examples include various siloxane or silicone compounds, e.g., hexamethyldisiloxane, amodimethicone, phenyltrimethicone, etc.

As yet another example, the surfactant may be a non-ionic surfactant. Examples include, but are not limited to polysorbates such as Polysorbate 20 (polyoxyethylene (20) sorbitan monolaurate), Polysorbate 40 (polyoxyethylene (20) sorbitan monopalmitate), Polysorbate 60 (polyoxyethylene (20) sorbitan monostearate), or Polysorbate 80 (polyoxyethylene (20) sorbitan monooleate), or sorbitan esters such as sorbitan monolaurate, sorbitan monopalmitate, sorbitan monostearate, sorbitan monooleate, sorbitan sesquioleate, sorbitan trioleate, or sorbitan isostearate.

In some embodiments, the second phase may comprise a polyglycol. The polyglycol may include a polyhydric alcohol of a monomeric glycol such as polyethylene glycol (PEG) and/or polypropylene glycol (PPG). For example, the PEG or PPG may be PEG or PPG 200, 300, 400, 600, 1,000, 1,450, 3,350, 4,000, 6,000, 8,000, and 20,000, where the number indicates the approximate average molecular weight of the PEG or PPG. As is understood by those of ordinary skill in the art, a polyglycol composition often will comprise a range of molecular weights, although the approximate average molecular weight is used to identify the type polyglycol. More than one PEG and/or PPG can also be present in certain instances.

More than one PEG and/or PPG can also be present in certain instances. The composition can include any suitable amount of polyglycol, for example, at least about 1 wt %, at least about 3 wt %, at least about 5 wt %, at least about 10 wt %, at least about 20 wt %, at least about 30 wt %, at least about 40 wt %, at least about 50 wt %, etc. In some cases, no more than about 60 wt %, no more than about 50 wt %, no more than about 40 wt %, no more than about 30 wt %, no more than about 20 wt %, no more than about 18 wt %, no more than about 15 wt %, no more than about 12 wt %, or no more than about 10 wt % of the composition is polyglycol. Combinations of any of these are also possible. For example, the composition may be between about 0 wt % and about 10 wt % polyglycol. The composition may include one or more than one type of polyglycol.

Additionally, purified water may be present in the second phase in some embodiments, although in other cases, little or no water is present in the second phase. For example, the first phase, the second phase, can contain less than 10%, less than 5%, less than 2%, less than 1%, or less that 0.05% (e.g., wt %) of water relative to the weight of the respective phase or of the entire composition. In some cases, the second phase may also comprise adjunct ingredients such as those described herein.

The second phase may include any one, or more than one, of the materials described above. In addition, any suitable amount of second phase can be used in accordance with various embodiments. For example, the second phase may be present at at least about 10 wt %, at least about 20 wt %, at least about 30 wt %, at least about 40 wt %, at least about 50 wt %, at least about 60 wt %, at least about 70 wt %, at least about 80 wt %, or at least about 90 wt % of the composition. In some cases, the ratio of the first phase (e.g., comprising phosphatidylcholine or lecithin) to the second phase can be at least about 1:3, at least about 1:2, at least about 1:1, at least about 2:1, at least about 3:1, or at least about 4:1, etc.

As a specific non-limiting example of one set of embodiments, a polyenylphosphatidylcholine comprises a certain material with the trade name NAT 8729, and optionally at least one polyglycol (e.g., PEG or PPG, such as is described herein). The composition can also comprise a PPC-enriched phosphatidylcholine material that is present within the first or second phase, e.g., comprising various components such as pyruvic acid, pyruvate, antioxidants such as those described herein, etc. The second phase may also comprise a surfactant such as a siloxylated polyether comprising dimethyl, methyl(propylpolyethylene oxide propylene oxide, acetate) siloxane commercially available from vendors such as Dow Corning (Dow Corning 190 surfactant) and lubricant such as silicone fluids containing low viscosity polydimethylsiloxane polymers, methylparaben (p-hydroxy benzoic acid methyl ester) commercially available from vendors such as Dow Corning (Dow Corning 200 silicone fluid).

Other examples of materials that can be used as (or within) the formulation include, but are not limited to, benzyl alcohol, ethyl alcohol, isopropyl palmitate (IPP), propanediol, and caprylic/capric triglycerides.

As another example, the first phase also comprises, in some embodiments, a fatty acid ester. Non-limiting examples include ascorbate palmitate or isopropyl palmitate. In some cases, the fatty acid ester is used as a preservative or an antioxidant. The composition can include any suitable amount of fatty acid ester, for example, at least about 1 wt %, at least about 3 wt %, at least about 5 wt %, at least about 10 wt %, at least about 20 wt %, at least about 30 wt %, at least about 40 wt %, at least about 50 wt %, etc. In some cases, no more than about 60 wt %, no more than about 50 wt %, no more than about 40 wt %, no more than about 30 wt %, no more than about 20 wt %, no more than about 18 wt %, no more than about 15 wt %, no more than about 12 wt %, or no more than about 10 wt % of the composition is fatty acid ester. Combinations of any of these are also possible. For example, the composition may be between about 0 wt % and about 10 wt % fatty acid ester. The composition may include one or more than one fatty acid ester.

In another set of embodiments, the composition may also include one or more transdermal penetration enhancers. Examples of transdermal penetration enhancers include, but are not limited to, 1,3-dimethyl-2-imidazolidinone or 1,2-propanediol. Other examples include cationic, anionic, or nonionic surfactants (e.g., sodium dodecyl sulfate, polyoxamers, etc.); fatty acids and alcohols (e.g., ethanol, oleic acid, lauric acid, liposomes, etc.); anticholinergic agents (e.g., benzilonium bromide, oxyphenonium bromide); alkanones (e.g., n-heptane); amides (e.g., urea, N,N-dimethyl-m-toluamide); organic acids (e.g., citric acid); sulfoxides (e.g., dimethylsulfoxide); terpenes (e.g., cyclohexene); ureas; sugars; carbohydrates or other agents. The transdermal penetration enhancers can be present in any suitable amount within the composition. For example, at least about 10 wt %, at least about 20 wt %, at least about 30 wt %, at least about 40 wt %, or at least about 50 wt % of the composition may comprise one or more transdermal penetration enhancers. In some cases, no more than about 60 wt %, no more than about 50 wt %, no more than about 40 wt %, no more than about 30 wt %, no more than about 20 wt %, no more than about 10 wt %, no more than about 9 wt %, or no more than about 5 wt % of the composition comprises transdermal penetration enhancers. Combinations of any of these are also possible. For example, the composition may have between about 0 wt % and about 5 wt % of one or more transdermal penetration enhancers.

In other embodiments, the composition may be modified in order to control depth of penetration. For example, in certain embodiments, the composition includes one or more polymers that act to reduce penetration depth of various components, etc. Controlled depth of penetration may be important for indications where local administration is desired without systemic effects. Examples of transdermal penetration barrier polymers include, but are not limited to, silicone waxes, acrylate polymers, and dimethicone copolymers. In certain embodiments, a transdermal penetration barrier polymer is nonionic. A transdermal penetration barrier polymer can be present in any suitable amount within the composition. For example, at least about 10 wt %, at least about 20 wt %, at least about 30 wt %, at least about 40 wt %, or at least about 50 wt % of the composition may comprise one or more transdermal penetration barrier polymers. In some cases, no more than about 60 wt %, no more than about 50 wt %, no more than about 40 wt %, no more than about 30 wt %, no more than about 20 wt %, no more than about 10 wt %, no more than about 9 wt %, or no more than about 5 wt % of the composition comprises a transdermal penetration barrier polymer. Combinations of any of these are also possible. For example, the composition may have between about 0 wt % and about 5 wt % of one or more transdermal penetration barrier polymers.

In some embodiments, various compositions are formulated to be substantially clear or substantially transparent. Transparency may be useful, for instance, for product acceptance in the marketplace, e.g., when applied to the skin of a subject. However, in other embodiments, the composition is not necessarily transparent. Certain substances can be useful in providing a substantially transparent composition, for example, fatty acid esters such as ascorbate palmitate or isopropyl palmitate. In one set of embodiments, the composition may be substantially transparent such that incident visible light (e.g., have wavelengths of between about 400 nm and about 700 nm) can be transmitted through 1 cm of the composition with a loss in intensity of no more than about 50%, about 60%, about 70%, about 80%, or about 90% relative to the incident light. In some embodiments, there may be no substantial difference in the wavelengths that are absorbed by the composition (i.e., white light passing through the composition appears white), although in other cases, there can be more absorption at various wavelengths (for example, such that white light passing through the composition may appear colored).

Other components may also be present within the composition, in accordance with certain embodiments. For example, the composition may include volatile organic fluids, fatty acids, volatile aromatic cyclic compounds, high molecular weight hydrocarbons, or the like.

As mentioned, in some embodiments, the components may be stable at room temperature. In some cases, the components may be released, for example, when the composition is exposed to an aqueous environment, e.g., within the body. Without wishing to be bound by any theory, it is believed that when the composition is applied to the skin, the liquid crystal structure collapses, delivering components to the skin or other desired area of treatment. The concentration of the components inside the liquid crystal matrix can be varied in terms of concentration. The matrix also may act as a sustained release delivery system in some embodiments. It is also believed that the liquid crystal is highly penetrating, such that the components can be delivered to the epidermis, dermis and dermal vascular for systemic release as well as to subcutaneous fat, at least under some conditions.

Thus, a composition such as is discussed herein may be prepared and/or stored at any suitable temperature and under any suitable conditions. In some embodiments, for instance, a composition can be prepared and/or stored under limited or no oxygen conditions. The composition can also be prepared and/or stored under limited or no nitrogen and/or carbon dioxide. For instance, the composition may be prepared and/or stored in a sealed environment (e.g., stored in a sealed container). The sealed environment (e.g., container) can be at least substantially devoid of gas, and/or contains a gaseous mixture that excludes, or at least is depleted in, oxygen. In some embodiments, an environment depleted in oxygen may have less than about 20%, less than about 15%, less than about 10%, less than about 5%, about 1% or less, about 0.1% or less, about 0.01% or less, about 0.001% or less, oxygen (e.g., as a wt % or as molar % per volume). For example, the gaseous mixture may include a noble gas, such as argon, helium, neon, etc. In one set of embodiments, the container may comprise a multi-layered metallic and/or polymeric barrier, e.g., formed from Glaminate® (American Can Company). For instance, the container may have the shape of a tube. Thus, in certain embodiments, the container is substantially resistant to oxygen permeation, nitrogen permeation, and/or carbon dioxide permeation. In certain embodiments, the container is substantially watertight, for example, such that substantially no water is absorbed by the container, or such that no water is able to pass through the container even if the container is filled with water.

In certain embodiments, the composition may be stored at temperatures of less than about 80° C., less than about 70° C., less than about 60° C., less than about 50° C., less than about 40° C., less than about 30° C., less than about 25° C., less than about 20° C., less than about 15° C., less than about 10° C., less than about 5° C., less than about 0° C., etc., for extended periods of time, e.g., at least about a day, at least about a week, at least about 4 weeks, at least about 2 months, at least about 3 months, at least about 4 months, at least about 6 months, at least about 1 year, at least about 2 years, at least about 3 years, etc.

In accordance with certain embodiments, a composition as discussed herein may be prepared by mixing at least a first phase and a second phase together. More than two phases may be combined in some cases. The second phase can comprise an emulsifier, or any other components discussed herein. The first phase may comprise a lecithin such as phosphatidylcholine and/or polyenylphosphatidylcholine, e.g., PPC-enriched phosphatidylcholine, for instance, as described herein. In some embodiments, other components are also mixed into the composition, for example, transdermal penetration enhancers, adjuvants, polyglycols (e.g., PEG and/or PPG), surfactants, lubricants, etc. as discussed herein.

In some embodiments, a composition may be prepared as discussed above, then diluted, e.g., with a diluent, to produce a final composition. For example, a "stock" composition may be initially prepared, then the stock composition diluted to produce a final composition, e.g., before use, before storage, before packaging, etc. In some embodiments, the diluent used may be a component as discussed herein (for example, forming at least a portion of the second phase), and the same or different materials than may be present in the initial composition may be used. The dilution ratio (amount of diluent added, relative to the initial composition) may be at least about 2, at least about 3, at least about 5, at least about 10, at least about 15, at least about 20, at least about 25, at least about 30, at least about 50, or at least about 100, or any other suitable factor.

A composition may be prepared and/or stored at any suitable temperature and under any suitable conditions. In some embodiments, for instance, a composition can be prepared and/or stored under limited or no oxygen conditions. The composition can also be prepared and/or stored under limited or no nitrogen and/or carbon dioxide. For instance, the composition may be prepared and/or stored in a sealed environment (e.g., stored in a sealed container). The sealed environment (e.g., container) can be at least substantially devoid of gas, and/or contains a gaseous mixture that excludes, or at least is depleted in, oxygen. In some embodiments, an environment depleted in oxygen may have less than about 20%, less than about 15%, less than about 10%, less than about 5%, about 1% or less, about 0.1% or less, about 0.01% or less, about 0.001% or less, oxygen (e.g., as a wt % or as molar % per volume). For example, the gaseous mixture may include a noble gas, such as argon, helium, neon, etc. In one set of embodiments, the container may comprise a multi-layered metallic and/or polymeric barrier, e.g., formed from Glaminate® (American Can Company). For instance, the container may have the shape of a tube. Thus, in certain embodiments, the container is substantially resistant to oxygen permeation, nitrogen permeation, and/or carbon dioxide permeation. In certain embodiments, the container is substantially watertight, for example, such that substantially no water is absorbed by the container, or such that no water is able to pass through the container even if the container is filled with water. In some cases, the composition may be prepared and/or stored under relatively low relative humidities (RH) (e.g., less than about 50% RH, less than about 40% RH, less than about 30% RH, less than about 20% RH, or less than about 10% RH), and/or in the presence of a suitable desiccant, such as phosphorous pentoxide or silica gel.

In certain aspects, a composition such as those described herein may be applied to the skin, e.g., for topical or transdermal delivery. In some cases, the composition is a cream, although other formulations are also possible in some instances, e.g., a liquid, a gel, a cream, a lotion, an ointment, a soap, a solid "stick," or the like, such as is discussed herein.

In some cases, the composition may a viscosity of at least about 1,000 cP, at least about 2,000 cP, at least about 3,000 cP, at least about 5,000 cP, at least about 7,000 cP, at least about 10,000 cP, at least about 12,000 cP, at least about 15,000 cP, at least about 20,000 cP, at least about 30,000 cP, at least about 40,000 cP, at least about 50,000 cP, at least about 60,000 cP, at least about 70,000 cP, or at least about 80,000 cP.

For example, in some embodiments, application of compositions such as those described herein may be applied to the skin of a subject, e.g., to increase fat deposits within the skin, and/or to rejuvenate the appearance of the skin. Additionally, in some embodiments, the composition may be applied in conjunction with other types of treatments to a subject, e.g., to the skin of a subject, for treatment of any of the diseases, conditions, or needs described herein. These may be occur, e.g., simultaneously or sequentially, in various embodiments. Thus, certain compositions as described herein may be used to treat a wide variety of diseases or conditions. To "treat" a disorder, as used herein, means to reduce or eliminate a sign or symptom of the disorder, to stabilize the disorder, to inhibit the disorder, and/or to reduce or slow further progression of the disorder. The subject may be a human subject, or a non-human mammal in some cases.

In certain cases, a composition such as those described herein can be administered to a subject, such as a human subject, by rubbing it on the skin, e.g., in areas located at or at least within the vicinity of a desired target area. Other areas have also been described herein, in other embodiments. Without wishing to be bound by any theory, it is believed that phosphatidylcholine provides or facilitates delivery of the compounds described herein to the skin, allowing the components to be delivered to a target area. In some embodiments, the composition can be applied by rubbing the composition against the skin, or to the mucosal surface, which allows the composition (or at least, the compounds described herein and/or related compounds) to be absorbed by the skin.

The composition can be applied once, or more than once. For example, the composition may be administered at predetermined intervals. In some embodiments, for instance, the composition may be applied once per day, twice per day, 3 times per day, 4 times per day, once every other day, once every three days, once every four days, etc. The amount or concentration of the compounds necessary to bring about the therapeutic treatment is not fixed per se, and may depend upon factors such as the desired outcome, the type and severity the disease or condition, the concentration of the compounds present within the composition, etc.

Thus, some embodiments provide methods of administering any composition such as discussed herein to a subject. When administered, the compositions are applied in a therapeutically effective, pharmaceutically acceptable amount as a pharmaceutically acceptable formulation. Any of the compositions may be administered to the subject in a therapeutically effective dose. When administered to a subject, effective amounts will depend on the particular condition being treated and the desired outcome. A therapeutically effective dose may be determined by those of ordinary skill in the art, for instance, employing factors such as those described herein and using no more than routine experimentation.

In certain embodiments, the administration of various compositions may be designed so as to result in sequential exposures to the composition over a certain time period, for example, hours, days, weeks, months, or years. This may be accomplished, for example, by repeated administrations of a composition by one or more of the methods described herein, or by a sustained or controlled release delivery system in which the composition is delivered over a prolonged period without repeated administrations. Administration of the composition using such a delivery system may be, for example, by a transdermal patch. Maintaining a substantially constant concentration of the composition may be preferred in some cases.

For certain chronic treatments or therapies, it is contemplated that a composition as discussed herein may be used to deliver the compounds described herein to the skin or mucosal surface at a relatively high concentration during an initial treatment, and the amount of may be lowered or "titrated" down to a relatively lower concentration maintenance dose or amount.

In one set of embodiments, compositions described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

In one set of embodiments, the dosage may be between about 0.01 mg and about 500 g, between about 0.01 mg and about 300 g, between about 0.01 mg and about 100 g, between about 0.01 mg and about 30 g, between about 0.01 mg and about 10 g, between about 0.01 mg and about 3 g, between about 0.01 mg and about 1 g, between about 0.01 mg and about 300 mg, between about 0.01 mg and about 100 mg, between about 0.01 mg and about 30 mg, between about 0.01 mg and about 10 mg, between about 0.01 mg and about 3 mg, between about 0.01 mg and about 1 mg, between about 0.01 mg and about 0.3 mg, or between about 0.01 mg and about 0.1 mg.

In another set of embodiments, the dosage may be at least about 0.01 mg, at least about 0.02 mg, at least about 0.03 mg, at least about mg, at least about 0.05 mg, at least about 0.1 mg, at least about 0.2 mg, at least about 0.3 mg, at least about 0.5 mg, at least about 1 mg, at least about 2 mg, at least about 3 mg, at least about 5 mg, at least about 10 mg, at least about 20 mg, at least about 30 mg, at least about 50 mg, at least about 100 mg, at least about 200 mg, at least about 300 mg, at least about 500 mg, at least about 1 g, at least about 2 g, at least about 3 g, at least about 5 g, at least about 10 g, etc. In some cases, the dosage may be no more than about 10 g, no more than about 5 g, no more than about 3 g, no more than about 2 g, no more than about 1 g, no more than about 500 mg, no more than about 300 mg, no more than about 200 mg, no more than about 100 mg, no more than about 50 mg, no more than about 30 mg, no more than about 20 mg, no more than about 10 mg, no more than about 5 mg, no more than about 3 mg, no more than about 2 mg, no more than about 1 mg, no more than about 0.5 mg, no more than about 0.3 mg, no more than about 0.2 mg, no more than about 0.1 mg, no more than about 0.05 mg, no more than about 0.03 mg, no more than about 0.02 mg, no more than about 0.01 mg, etc. In some cases, combinations of any of these are also possible, e.g., between about 0.01 mg and about 0.1 mg.

The compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent. In certain embodiments, the additional therapeutic agent is present in a provided composition in addition to the compounds described herein. In other embodiments, the additional therapeutic agent is administered separately from the compositions described herein.

When co-administered with other agents, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed.

In certain embodiments, a composition comprising compounds as described herein, and the additional therapeutic agent are each administered in an effective amount (i.e., each in an amount which would be therapeutically effective if administered alone). In other embodiments, a composition comprising compounds as described herein, and the additional therapeutic agent are each administered in an amount which alone does not provide a therapeutic effect (a sub-therapeutic dose). In yet other embodiments, a composition comprising compounds as described herein can be administered in an effective amount, while the additional therapeutic agent is administered in a sub-therapeutic dose. In still other embodiments, a composition comprising compounds as described herein can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of a composition as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound. For example, a composition as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

More specifically, a first therapy (e.g., a prophylactic or therapeutic agent such as a composition described herein)

can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

In one set of embodiments, a composition such as is discussed herein may be applied to the skin or mucosal surface of a subject, e.g., at any suitable location. The composition may be contacted using any suitable method. For example, the composition may be rubbed on, poured on, applied with an applicator (e.g., a gauze pad, a swab, a bandage, etc.), or the like. In some cases, the composition can be a liquid, a gel, a cream, a lotion, an ointment, a solid "stick," or the like, that can be applied to the skin or mucosal surface by hand, for example, by rubbing or spraying. The composition may be applied to any suitable surface of the subject, e.g., the head, neck, arms, or legs. In addition, in certain embodiments, the composition is applied to a mucosal surface of the subject. For example, the composition may be applied to the nose or nostrils, the mouth, the lips, the eyelids, the ears, the genital area (of either male or female subjects), or the anus.

The compositions may additionally comprise one or more adjunct ingredients, for instance, pharmaceutical drugs or skin care agents. For example, compositions may include adjuvants such as salts, buffering agents, diluents, excipients, chelating agents, fillers, drying agents, antioxidants, antimicrobials, preservatives, binding agents, bulking agents, silicas, solubilizers, or stabilizers. Non-limiting examples include species such as calcium carbonate, sodium carbonate, lactose, kaolin, calcium phosphate, or sodium phosphate; granulating and disintegrating agents such as corn starch or algenic acid; binding agents such as starch, gelatin or acacia; lubricating agents such as magnesium stearate, stearic acid, or talc; time-delay materials such as glycerol monostearate or glycerol distearate; suspending agents such as sodium carboxymethylcellulose, methylcellulose, hydroxypropylmethylcellulose, sodium alginate, polyvinylpyrrolidone; dispersing or wetting agents such as lecithin or other naturally-occurring phosphatides; thickening agents such as cetyl alcohol or beeswax; buffering agents such as acetic acid and salts thereof, citric acid and salts thereof, boric acid and salts thereof, or phosphoric acid and salts thereof; or preservatives such as benzalkonium chloride, chlorobutanol, parabens, or thimerosal. Suitable concentrations can be determined by those of ordinary skill in the art, using no more than routine experimentation. Those of ordinary skill in the art will know of other suitable formulation ingredients, or will be able to ascertain such, using only routine experimentation.

Preparations can include sterile aqueous or nonaqueous solutions, suspensions and emulsions, which can be isotonic with the blood of the subject in certain embodiments. Examples of nonaqueous solvents are polypropylene glycol, polyethylene glycol, vegetable oil such as olive oil, sesame oil, coconut oil, *arachis* oil, peanut oil, mineral oil, organic esters such as ethyl oleate, or fixed oils including synthetic mono or di-glycerides. Aqueous solvents include water, alcoholic/aqueous solutions, emulsions or suspensions, including saline and buffered media. Parenteral vehicles include sodium chloride solution, 1,3-butandiol, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents and inert gases and the like. Those of skill in the art can readily determine the various parameters for preparing and formulating the compositions without resort to undue experimentation.

In some embodiments, a composition such as described herein may be applied to a surgical device, tool, or other substrate. For example, a composition may be applied to sutures, implants, surgical tools, or other substrates that may come into contact with wounded tissue (e.g., cut tissue) during surgery. In some embodiments, a composition may be provided as a cream or ointment as described in more detail herein. It also should be appreciated that certain compositions may be provided on surgical dressings, bandages, or other material that is to be contacted to a surgical wound.

In one set of embodiments, a composition such as is described herein may be applied to a material or substrate immediately prior to use on a subject. However, in some embodiments, a material or substrate may be prepared (e.g., packaged, stored, or otherwise prepared) to contain a composition prior to use. For example, prepackaged bandages or surgical devices, sutures, or implants may be prepared and packaged with a coating of a composition such as is described herein. Compositions may be used for human or other animal subjects.

In another aspect, the present disclosure is directed to a kit including one or more of the compositions discussed herein. A "kit," as used herein, typically defines a package or an assembly including one or more of the compositions, and/or other compositions, for example, as described herein. Each of the compositions of the kit may be provided in liquid form (e.g., in solution), or in solid form (e.g., a dried powder). In certain cases, some of the compositions may be constitutable or otherwise processable (e.g., to an active form), for example, by the addition of a suitable solvent or other species, which may or may not be provided with the kit. Examples of other compositions or components include, but are not limited to, solvents, surfactants, diluents, salts, buffers, chelating agents, fillers, antioxidants, binding agents, bulking agents, preservatives, drying agents, antimicrobials, needles, syringes, packaging materials, tubes, bottles, flasks, beakers, dishes, frits, filters, rings, clamps, wraps, patches, containers, and the like, for example, for using, administering, modifying, assembling, storing, packaging, preparing, mixing, diluting, and/or preserving the compositions components for a particular use, for example, to a sample and/or a subject.

A kit may, in some cases, include instructions in any form that are provided in connection with compositions such as those discussed herein in such a manner that one of ordinary skill in the art would recognize that the instructions are to be associated with the compositions. For instance, the instructions may include instructions for the use, modification, mixing, diluting, preserving, administering, assembly, storage, packaging, and/or preparation of the composition and/or other compositions associated with the kit. In some cases, the instructions may also include instructions for the delivery and/or administration of the compositions, for example, for a particular use, e.g., to a sample and/or a subject. The instructions may be provided in any form recognizable by one of ordinary skill in the art as a suitable vehicle for containing such instructions, for example, written or published, verbal, audible (e.g., telephonic), digital, optical, visual (e.g., videotape, DVD, etc.) or electronic communications (including Internet or web-based communications), provided in any manner.

The following documents are incorporated herein by reference: U.S. Pat. No. 8,668,937, issued Mar. 11, 2014, entitled "Topical Nitric Oxide Systems and Methods of Use Thereof"; U.S. Pat. No. 8,435,942, issued Apr. 26, 2006, entitled "Methods for Formulating Stabilized Insulin Compositions"; U.S. Pat. No. 7,182,956, issued Feb. 27, 2007, entitled "Stable Topical Drug Delivery Compositions"; U.S. Pat. No. 8,273,711, issued Sep. 25, 2012, entitled "Topical Drug Delivery Using Phosphatidylcholine"; U.S. patent application Ser. No. 13/801,402, filed Mar. 13, 2013, entitled "Systems and Methods for Delivery of Peptides"; U.S. patent application Ser. No. 13/801,446, filed Mar. 13, 2013, entitled "Treatment of Skin, Including Aging Skin, to Improve Appearance"; U.S. patent application Ser. No. 13/801,488, filed Mar. 13, 2013, entitled "Hair Treatment Systems and Methods Using Peptides and Other Compositions"; U.S. patent application Ser. No. 13/801,518, filed Mar. 13, 2013, entitled "Skin Tanning Using Peptides and Other Compositions"; U.S. patent application Ser. No. 13/801,543, filed Mar. 13, 2013, entitled "Topical Systems and Methods for Treating Sexual Dysfunction"; U.S. patent application Ser. No. 13/800,952, filed Mar. 13, 2013, entitled "Immune Modulation Using Peptides and Other Compositions"; U.S. patent application Ser. No. 13/801,013, filed Mar. 13, 2013, entitled "Cardiovascular Disease Treatment and Prevention"; U.S. patent application Ser. No. 13/801,061, filed Mar. 13, 2013, entitled "Wound Healing Using Topical Systems and Methods"; U.S. patent application Ser. No. 13/801,110, filed Mar. 13, 2013, entitled "Peptide Systems and Methods for Metabolic Conditions"; U.S. patent application Ser. No. 13/801,188, filed Mar. 13, 2013, entitled "Methods and Systems for Treating or Preventing Cancer"; U.S. patent application Ser. No. 13/801,240, filed Mar. 13, 2013, entitled "Compositions and Methods for Affecting Mood States"; U.S. patent application Ser. No. 13/801,298, filed Mar. 13, 2013, entitled "Improvement of Memory or Learning Using Peptide and Other Compositions"; U.S. patent application Ser. No. 13/801,345, filed Mar. 13, 2013, entitled "Brain and Neural Treatments Comprising Peptides and Other Compositions"; U.S. patent application Ser. No. 13/019,101, filed Feb. 1, 2011, entitled "Method of Delivering Stable Topical Drug Compositions"; U.S. patent application Ser. No. 13/926,688, filed Jun. 25, 2013, entitled "Topical Drug Delivery Using Phosphatidylcholine"; Int. Pat. Apl. Ser. No. PCT/US2014/025822, filed Mar. 13, 2014, entitled "Treatment of Skin, Including Aging Skin, to Improve Appearance"; Int. Pat. Apl. Ser. No. PCT/US2014/025913, filed Mar. 13, 2014, entitled "Immune Modulation Using Peptides and Other Compositions"; Int. Pat. Apl. Ser. No. PCT/US2014/025996, filed Mar. 13, 2014, entitled "Cardiovascular Disease Treatment and Prevention"; Int. Pat. Apl. Ser. No. PCT/US2014/025572, filed Mar. 13, 2014, entitled "Wound Healing Using Topical Systems and Methods"; Int. Pat. Apl. Ser. No. PCT/US2014/025630, filed Mar. 13, 2014, entitled "Peptide Systems and Methods for Metabolic Conditions"; Int. Pat. Apl. Ser. No. PCT/US2014/025758, filed Mar. 13, 2014, entitled "Methods and Systems for Treating or Preventing Cancer"; Int. Pat. Apl. Ser. No. PCT/US2014/025898, filed Mar. 13, 2014, entitled "Improvement of Memory or Learning Using Peptide and Other Compositions"; Int. Pat. Apl. Ser. No. PCT/US2014/025820, filed Mar. 13, 2014, entitled "Brain and Neural Treatments Comprising Peptides and Other Compositions"; and Int. Pat. Apl. Ser. No. PCT/US2014/025705, filed Mar. 13, 2014, entitled "Systems and Methods for Delivery of Peptides."

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When the word "about" is used herein in reference to a number, it should be understood that still another embodiment of the disclosure includes that number not modified by the presence of the word "about."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A method, comprising:
applying, to the skin of a subject, a topical composition comprising a non-substituted humanin and lecithin, wherein the composition has a liquid crystal structure.

2. The method of claim 1, wherein the humanin comprises a 21-amino acid humanin.

3. The method of claim 2, wherein the 21-amino acid humanin has a sequence MAPRGFSCLLLLTSEIDLPVK (SEQ ID NO: 1).

4. The method of claim 1, wherein the humanin comprises a 24-amino acid humanin.

5. The method of claim 4, wherein the 24-amino acid humanin has a sequence MAPRGFSCLLLLT-SEIDLPVKRRA (SEQ ID NO: 2).

6. The method of claim 1, wherein the composition further comprises tributyrin.

7. The method of claim 1, wherein the composition further comprises 2,6-dimethyl-L-tyrosine.

8. The method of claim 1, wherein the lecithin is present at least about 0.25% by weight.

9. The method of claim 1, wherein the composition further comprises polyenylphosphatidylcholine.

10. The method of claim 1, wherein the composition comprises no more than about 250 ppm of water by weight of the composition.

11. The method of claim 1, wherein the composition further comprises a fatty acid ester.

12. The method of claim 1, wherein the composition further comprises a transdermal penetration enhancer.

13. The method of claim 1, wherein the composition is stable at room temperature.

14. A method, comprising:
applying, to the skin of a subject, a topical composition comprising a humanin-related peptide and lecithin, wherein the humanin-related peptide has a length of 21 amino acids or 24 amino acids, wherein the composition has a liquid crystal structure.

15. The method of claim 14, wherein the humanin-related peptide comprises HNG.

16. The method of claim 15, wherein the HNG has a sequence MAPRGFSCLLLLTGEIDLPVK (SEQ ID NO: 3).

17. The method of claim 15, wherein the HNG has a sequence MAPRGFSCLLLLTGEIDLPVKRRA (SEQ ID NO: 4).

18. A method, comprising:
applying, to the skin of a subject, a topical composition comprising a mitochondrial-derived peptide and lecithin, wherein the mitochondrial-derived peptide has a length of 21 amino acids or 24 amino acids, wherein the composition has a liquid crystal structure.

* * * * *